(12) United States Patent
Kim

(10) Patent No.: US 10,183,102 B2
(45) Date of Patent: Jan. 22, 2019

(54) HANDS-FREE BREAST PUMP

(71) Applicant: Sang Ha Kim, Seongnam-si (KR)

(72) Inventor: Sang Ha Kim, Seongnam-si (KR)

(*) Notice: Subject to any disclaimer, the term of this patent is extended or adjusted under 35 U.S.C. 154(b) by 0 days.

(21) Appl. No.: 15/501,857

(22) PCT Filed: Jul. 13, 2015

(86) PCT No.: PCT/KR2015/007241
§ 371 (c)(1),
(2) Date: Feb. 6, 2017

(87) PCT Pub. No.: WO2016/208800
PCT Pub. Date: Dec. 29, 2016

(65) Prior Publication Data
US 2017/0216505 A1    Aug. 3, 2017

(30) Foreign Application Priority Data
Jun. 25, 2015 (KR) .................. 10-2015-0090548

(51) Int. Cl.
*A61M 1/06* (2006.01)
(52) U.S. Cl.
CPC .............. *A61M 1/064* (2014.02); *A61M 1/06* (2013.01)
(58) Field of Classification Search
CPC ................................ A61M 1/064; A61M 1/06
See application file for complete search history.

(56) References Cited

U.S. PATENT DOCUMENTS

| 6,090,065 | A  | * | 7/2000  | Giles ................... A61M 1/062 |
|           |    |   |         | 604/315 |
| 6,764,377 | B2 |   | 7/2004  | Gillan |
| 8,137,153 | B2 |   | 3/2012  | Bell |
| 8,192,247 | B2 |   | 6/2012  | Abbaszadeh |
| 8,307,463 | B2 |   | 11/2012 | Ritchie |
| 8,500,679 | B2 |   | 8/2013  | Holshouser et al. |
| 8,702,646 | B2 |   | 4/2014  | Garbez et al. |
| 8,945,046 | B2 |   | 2/2015  | Brittner |
| 2017/0119942 | A1 | * | 5/2017 | Brittner ................ A61M 1/064 |

FOREIGN PATENT DOCUMENTS

| KR | 10-0390618 B1 | 7/2003 |
| KR | 10-0947668 B1 | 3/2010 |
| KR | 10-2010-0103152 A | 9/2010 |

(Continued)

OTHER PUBLICATIONS

International Search Report for PCT/KR2015/007241 dated Mar. 11, 2016 from Korean Intellectual Property Office.

*Primary Examiner* — Imani Hayman
(74) *Attorney, Agent, or Firm* — Revolution IP, PLLC

(57) ABSTRACT

A hands-free breast pump comprises a funnel-shaped adsorption unit having an adsorption surface and a suction tank; a suction chamber having an extension part, the extension part having a connection pipe and a second suction hole formed on the lower portion of the inner peripheral surface, and a first coupling part extended downwardly from the extension part and having a third suction hole formed on the lower portion of the inner peripheral surface thereof; and a storage vessel coupled to the first coupling part in the horizontal direction with the adsorption surface to store the breast milk discharged from the backflow prevention unit therein.

4 Claims, 16 Drawing Sheets

(56) References Cited

FOREIGN PATENT DOCUMENTS

| | | |
|---|---|---|
| KR | 10-2011-0009666 A | 1/2011 |
| KR | 10-1016662 B1 | 2/2011 |
| KR | 10-1244141 B1 | 3/2013 |
| KR | 10-2013-0118327 A | 10/2013 |
| KR | 10-1333536 B1 | 11/2013 |
| KR | 20-0469719 Y1 | 11/2013 |

* cited by examiner

HANDS-FREE BREAST PUMP

CROSS REFERENCE TO PRIOR APPLICATIONS

This application is a National Stage Application of PCT International Patent Application No. PCT/KR2015/007241 filed on Jul. 13, 2015, under 35 U.S.C. § 371, which claims priority to Korean Patent Application No. 10-2015-0090548 filed Jun. 25, 2015 which are all hereby incorporated by reference in their entirety.

TECHNICAL FIELD

The present invention relates to a breast pump and, more particularly, to a hands-free breast pump that is worn on a mother's breast to freely conduct breast pumping, without being taken by her hands.

BACKGROUND ART

A pregnant woman has full breasts through the change from colostrum to mature milk for a first week after giving birth, and next, the quantity of the breast milk is gradually decreased within three to five days. If the breast milk is not fed to her baby, her breasts become hard and hot painfully, which is developed to breast engorgement. So as to prevent the breast engorgement of the mother, breastfeeding should be frequently carried out 8 to 12 times per day, and if the breastfeeding is not conducted at a proper time, the breast milk should be forcedly expressed from her breasts. So as to forcedly express the breast milk from the breasts, breast pumps (or milking machines) are generally used.

Generally, the breast pump is a device for forcedly expressing the colostrum produced after delivery or the breast milk remaining after the breastfeeding. In accordance with the pumping types of the breast milk, the breast pump is classified into a manual breast pump for expressing breast milk through the compression of a pipette-shaped vacuum ball and an automatic breast pump for expressing breast milk through an electric pump. In case of the manual breast pump, the pipette-shaped vacuum ball is pressurized periodically by one hand, and a funnel-shaped adsorption unit coming into contact with the mother's breast is taken by the other hand, so that the breast milk is expressed from the breast. However, a quantity of breast milk pumped is relatively small and a large force is consumed to express the breast milk from the breast. Recently, the automatic breast pump has been widely prevailed.

In the same manner as the manual breast pump, however, the automatic breast pump has inconveniences in use because the funnel-shaped adsorption unit should be taken by one hand during the breast pumping, so that she does not do anything during the breast pumping. Further, both of the manual breast pump and the automatic breast pump are used in the state where the mother's body is exposed to the outside, and accordingly, they are used only in her house or given place and cannot be used in other places, thereby having many limitations in the use thereof.

So as to solve the above-mentioned problems, there have been proposed hands-free breast pumps having various structures coupled to bras in such a manner as to be worn on a mother's breast to freely conduct breast pumping, without being taken by her hands, and for example, such hands-free breast pumps are disclosed in Korean Patent No. 10-0947668 (dated on Mar. 8, 2010), Korean Patent No. 10-1333536 (dated on Nov. 21, 2013), U.S. Pat. No. 8,137,153 (dated on Mar. 20, 2012), U.S. Pat. No. 8,307,453 (dated on Nov. 13, 2012), U.S. Pat. No. 6,764,377 (dated on Jul. 20, 2004), U.S. Pat. No. 8,192,247 (dated on Jun. 5, 2012), and U.S. Pat. No. 8,500,679 (dated on Aug. 6, 2013).

According to the conventional hands-free breast pumps, however, a strap or a bra-shaped structure is needed to allow an adsorption unit to come into contact with a mother's breast during breast pumping, thereby increasing the volume of the breast pump, and some of the hands-free breast pumps require the breast pump-only bras or other clothes, thereby raising the cost for purchasing the breast pump. In case of some of the hands-free breast pumps, further, a hole is punched in the bra to allow the adsorption unit to come into contact with the mother's breast, and a breast milk vessel is located at the outside of the bra, so that as the quantity of breast milk pumped is increased, the breast milk vessel becomes inclined forwardly, and accordingly, if the breast milk is stored by given quantity in the breast milk vessel, the breast milk vessel should be taken by her hand, thereby still having the inconveniences in use thereof.

On the other hand, other conventional hands-free breast pumps are disclosed in U.S. Pat. No. 8,702,646 (dated on Apr. 22, 2014) and Korean Patent Application Laid-open No. 10-2011-0009666 (dated on Jan. 28, 2011), wherein the breast pump is located at the inside of the bra of the mother, without having any bra-shaped fixing device, thereby lowering the manufacturing cost thereof and removing the inconveniences in use thereof. In case of the hands-free breast pump as disclosed in U.S. Pat. No. 8,702,646, however, an adhesive material is additionally needed to allow the adsorption unit to come into contact with the mother's breast, thereby raising the manufacturing cost thereof, and in case of the hands-free breast pump as disclosed in Korean Patent Application Laid-open No. 10-2011-0009666, an attaching force to the mother's breast is relatively weak, thereby still having the inconveniences in use thereof.

DISCLOSURE

Technical Problem

Accordingly, the present invention has been made in view of the above-mentioned problems occurring in the prior art, and it is an object of the present invention to provide a hands-free breast pump that is worn on a mother's breast in such a manner as to be fixed to a bra, thereby freely conducting breast pumping, without being taken by her hands.

Technical Solution

To accomplish the above-mentioned object, according to the present invention, there is provided a hands-free breast pump including: a funnel-shaped adsorption unit having an adsorption surface adapted to come into contact with a mother's breast and a suction tank protruding backwardly from the adsorption surface in a vertical direction with respect to the adsorption surface and having a first suction hole formed on the lower portion of the inner peripheral surface thereof in a horizontal direction with respect to the adsorption surface; a suction chamber having an extension part adapted to be insertingly coupled to the rear portion of the suction tank, the extension part having a connection pipe disposed on one side of the top portion thereof in such a manner as to be connected to a suction line and a second suction hole formed on the lower portion of the inner peripheral surface thereof in such a manner as to be formed in a horizontal direction with respect to the adsorption surface or formed inclined backwardly by a given angle of about 20 to 50°, and a first coupling part extended downwardly from the extension part and having a third suction hole formed thereon to communicate with the second suction hole; a backflow prevention unit coupled to the lower periphery of the first coupling part; and a storage vessel coupled to the lower periphery of the first coupling part in such a manner as to be disposed in parallel with the adsorption surface in the horizontal direction with the adsorption surface or to be disposed inclined backwardly by a given angle of about 20 to 50° from the adsorption surface so as to store the breast milk discharged from the backflow prevention unit therein.

According to the present invention, desirably, the first coupling part includes a first connector having the third suction hole and a second connector disposed to surround the outer periphery of the first connector therewith in such a manner as to be spaced apart from the first connector by a given distance and coupled to the top periphery of the storage vessel, and the backflow prevention unit includes a second coupling part screw-fastened to the first connector and a pair of backflow prevention films disposed on the underside of the second coupling part to prevent the breast milk stored in the storage vessel from flowing back to the suction chamber.

According to the present invention, desirably, the adsorption unit further includes an alignment piece formed on the rear side of the suction tank in such a manner as to be fitted to an alignment groove formed at the inside of the extension part of the suction chamber, the alignment piece having a generally semi-circular or semi-oval shape, and correspondingly, the alignment groove having a semi-circular or semi-oval shape, so that in the state where the alignment piece is insertedly coupled to the alignment groove, the suction chamber is fixed to the suction tank, without being rotated.

According to the present invention, desirably, the suction chamber includes a connection part adapted to connect the extension part and the first coupling part to each other in such a manner as to allow the second suction hole and the third suction hole to vertically communicate with each other, the outer diameter of the connection part being smaller than the inner diameter of the third suction hole and the inner diameter of the connection part being the same as the inner diameter of the second suction hole.

According to the present invention, desirably, the hands-free breast pump further includes: a front cover coupled to the adsorption unit on the center thereof; and a rear cover having the front surface detachably coupled to the rear surface of the front cover and the rear surface having a given curved surface, the rear cover having an insertion slot formed on the lower portion thereof in such a manner as to insert the storage vessel thereinto in the state where the front cover and the rear cover are coupled to each other and to allow the storage vessel to be stably coupled to the first coupling part.

Advantageous Effects

According to the present invention, the hands-free breast pump is configured wherein the adsorption unit coming into contact with the mother's breast and the storage vessel storing the breast milk discharged through the adsorption unit therein are located in the horizontal direction with respect to each other, or the storage vessel is inclined backwardly from the adsorption unit by the given angle, so that the hands-free breast pump is stably fixed to the mother's breast through the bra in the state of coming into close contact with her breast, thereby freely conducting the breast pumping, without being taken by her hands.

BEST MODE FOR INVENTION

Figure 1:
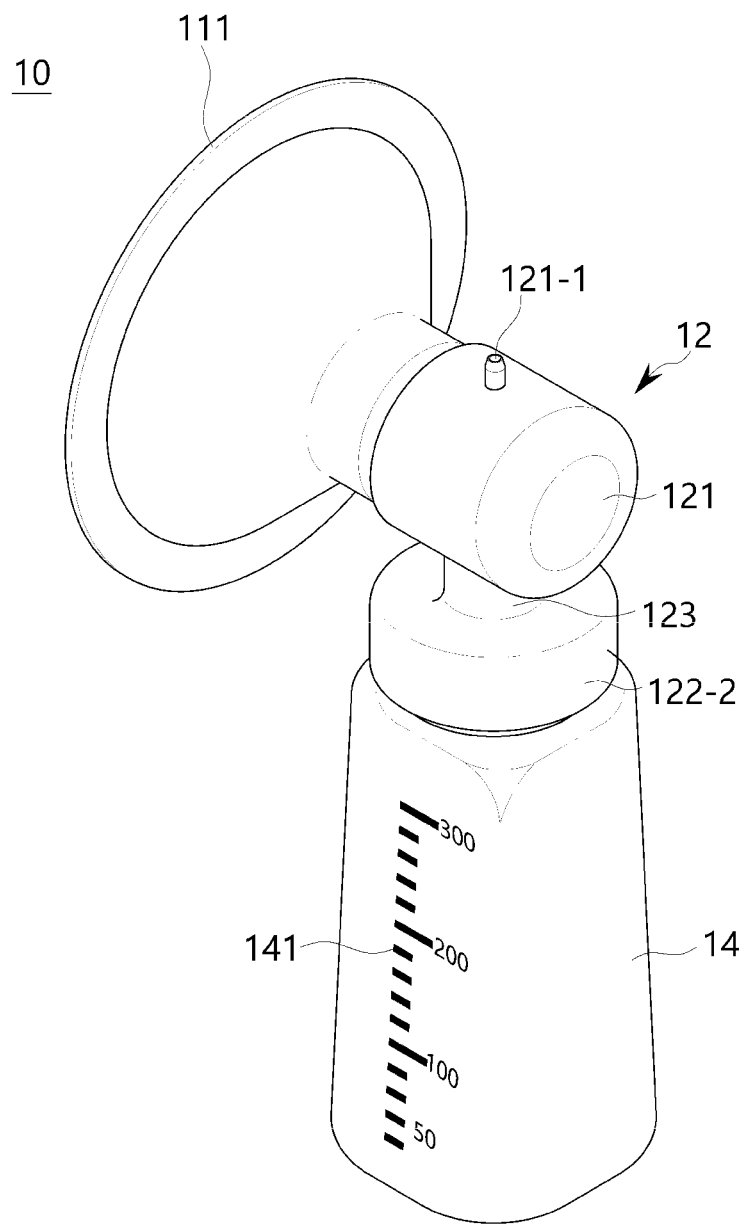
FIG. 1 is a perspective view showing the assembled state of a hands-free breast pump according to a first embodiment of the present invention.

The present invention relates to a hands-free breast pump including: a funnel-shaped adsorption unit having an adsorption surface adapted to come into contact with a mother's breast and a suction tank protruding backwardly from the adsorption surface in a vertical direction with respect to the adsorption surface and having a first suction hole formed on the lower portion of the inner peripheral surface thereof in a horizontal direction with respect to the adsorption surface; a suction chamber having an extension part adapted to be insertingly coupled to the rear portion of the suction tank, the extension part having a connection pipe disposed on one side of the top portion thereof in such a manner as to be connected to a suction line and a second suction hole formed on the lower portion of the inner peripheral surface thereof in such a manner as to be formed in a horizontal direction with respect to the adsorption surface or formed inclined backwardly by a given angle of about 20 to 50°, and a first coupling part extended downwardly from the extension part and having a third suction hole formed thereon to communicate with the second suction hole; a backflow prevention unit coupled to the lower periphery of the first coupling part; and a storage vessel coupled to the lower periphery of the first coupling part in such a manner as to be disposed in parallel with the adsorption surface in the horizontal direction with the adsorption surface or to be disposed inclined backwardly by a given angle of about 20 to 50° from the adsorption surface so as to store the breast milk discharged from the backflow prevention unit therein.

MODE FOR INVENTION

Objects, characteristics and advantages of the present invention will be more clearly understood from the detailed description as will be described below and the attached drawings. Before the present invention is disclosed and described, however, it is to be understood that the disclosed embodiments are merely exemplary of the invention, which can be embodied in various forms.

Therefore, specific structural and functional details disclosed herein are not to be interpreted as limiting, but merely as a basis for the claims and as a representative basis for teaching one of ordinary skill in the art to variously employ the present invention in virtually any appropriately detailed structure.

In the description, further, the corresponding parts in the embodiments of the present invention are indicated by corresponding reference numerals. Also, the terms used (mentioned) herein is for the purpose of describing particular embodiments only and is not intended to be limiting. The term 'a' or 'an', as used herein, are defining as one or more than one. The term 'including' and/or 'having', as used herein are intended to refer to the above elements and operations, and it is to be understood that the terms are not intended to preclude the presence of one or more elements and operations and added possibilities.

All terms (including technical or scientific terms), used herein, unless otherwise defined, have the same meanings which are typically understood by those having ordinary skill in the art. The terms, such as ones defined in common dictionaries, should be interpreted as having the same meanings as terms in the context of pertinent technology, and should not be interpreted as having ideal or excessively formal meanings unless clearly defined in the specification.

Hereinafter, an explanation on the technical characteristics of a hands-free breast pump according to preferred embodiments of the present invention will be in detail given with reference to the attached drawing.

Figure 2:
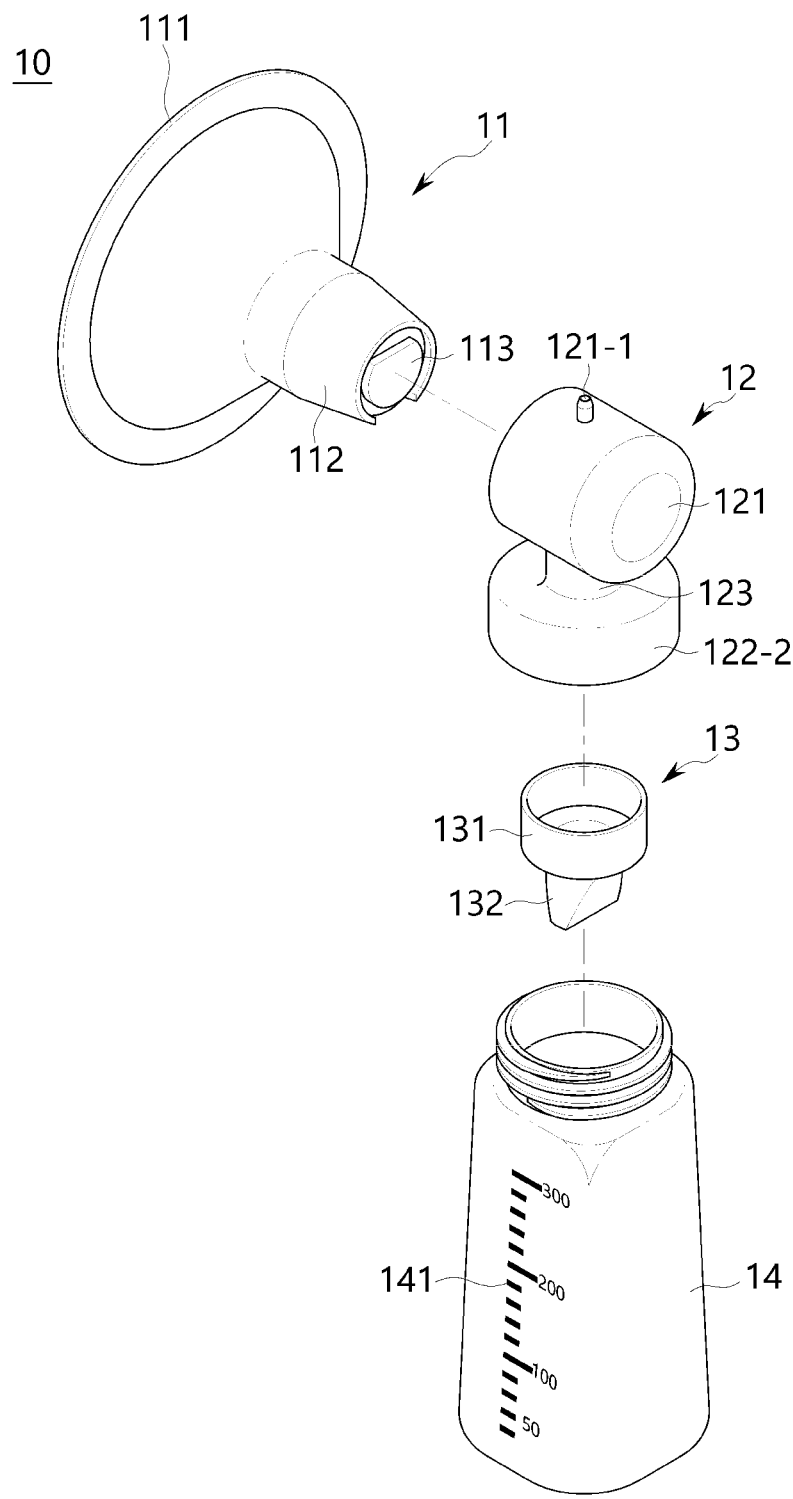
FIG. 2 is an exploded perspective view showing the hands-free breast pump of FIG. 1.
Figure 3:
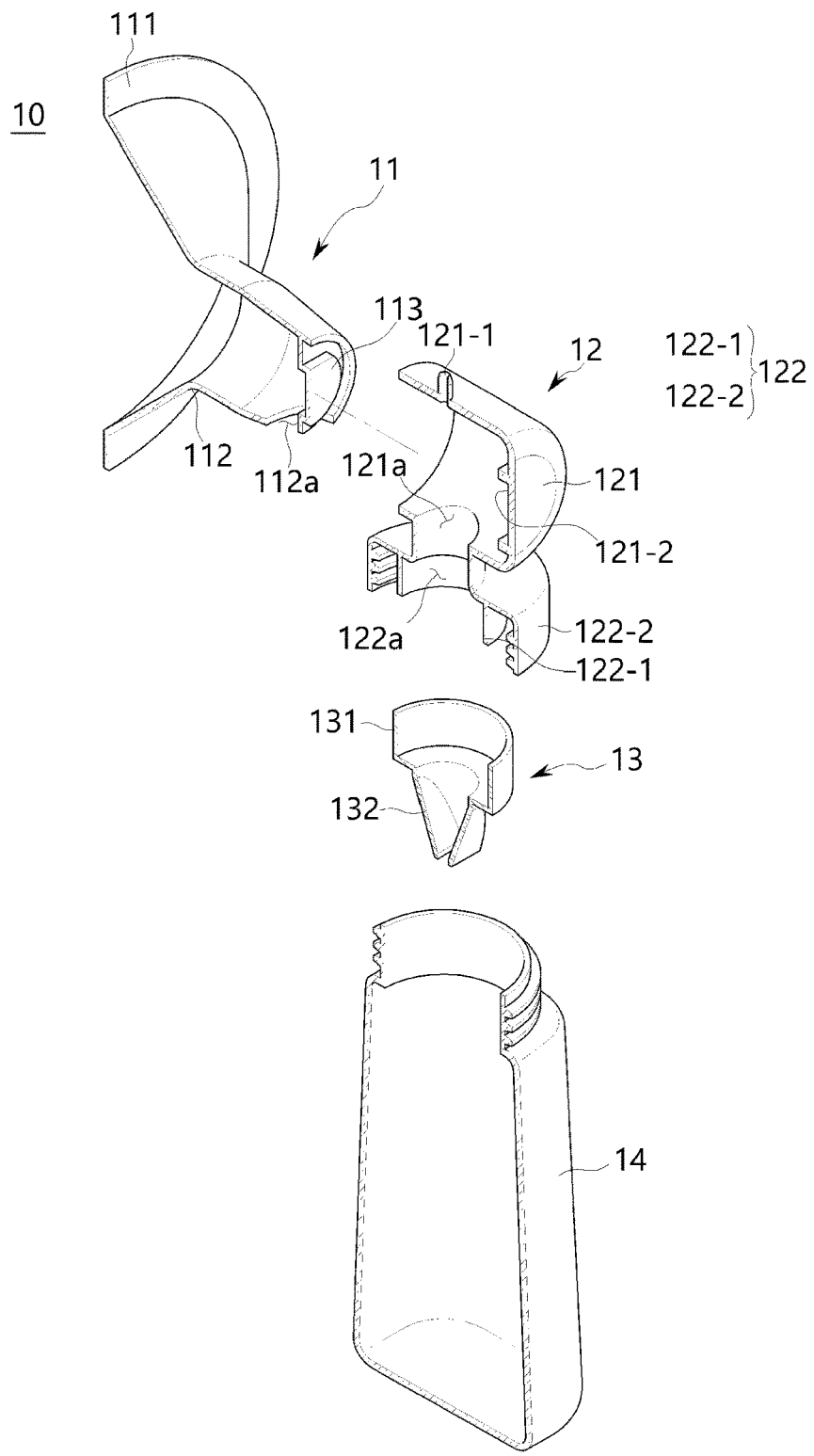
FIG. 3 is a sectional perspective view showing the hands-free breast pump of FIG. 2 cut off in an up and down direction thereof.

FIG. 1 is a perspective view showing the assembled state of a hands-free breast pump according to a first embodiment of the present invention, FIG. 2 is an exploded perspective view showing the hands-free breast pump of FIG. 1, and FIG. 3 is a sectional perspective view showing the hands-free breast pump of FIG. 2 cut off in an up and down direction thereof.

As shown in FIGS. 1 to 3, a hands-free breast pump 10 according to a first embodiment of the present invention includes an adsorption unit 11, a suction chamber 12, a backflow prevention unit 13 and a storage vessel 14.

As shown in FIGS. 2 and 3, the adsorption unit 11 takes a shape of a funnel or cup in such a manner as to be depressed backwardly to accommodate a mother's breast therein and includes an adsorption surface 111 adapted to come into contact with the mother's breast. At this time, the adsorption surface 111 is made of a flexible material capable of corresponding to the shape of a woman's breast. For example, the adsorption surface 111 is made of silicone rubber.

Further, the adsorption unit 11 includes a suction tank 112 protruding backwardly from the adsorption surface 111. As shown in FIG. 3, the suction tank 112 is extended vertically from the adsorption surface 111 and has a shape of a tank empty in the interior thereof. The suction tank 112 has a first suction hole 112a formed on the lower portion of the inner peripheral surface thereof in a horizontal direction with respect to the adsorption surface 111, that is, in a vertical direction with respect to the protruding direction of the suction tank 112. Accordingly, the breast milk pumped from the mother's breast is transmitted to the suction chamber 12 through the first suction hole 112a of the suction tank 112.

As shown in FIGS. 2 and 3, the suction chamber 12 is connected to an electric pump 1 (or a manual pump like a pipette-shaped vacuum ball) by means of a suction line 2 (See FIG. 7) and is vacuumed by the operation of the electric pump (See FIG. 7), so that the mother's breast accommodated in the adsorption unit 11 becomes compressed by means of the pressure difference generated in the interior of the suction chamber 12, thereby allowing the breast milk to be expressed from the breast.

As shown in FIGS. 2 and 3, the suction chamber 12 includes an extension part 121 adapted to be insertingly coupled to the rear portion of the suction tank 112. The extension part 121 has a connection tube 121-1 disposed on one side of the top portion thereof in such a manner as to be connected to the suction line 2 and a second suction hole 121a formed on the lower portion of the inner peripheral surface thereof in such a manner as to be aligned vertically to the first suction hole 112a of the suction tank 112 to communicate with the first suction hole 112a.

As shown in FIG. 3, the suction chamber 12 further has a first coupling part 122 extended downwardly from the extension part 121 in a vertical direction with respect to the extension part 121 in such a manner as to be coupled to the backflow prevention unit 13 and the storage vessel 14 and having a third suction hole 122a formed on the lower portion of the inner peripheral surface thereof in such a manner as to be aligned vertically to the second suction hole 121a to communicate with the second suction hole 121a.

Further, as shown in FIG. 2, the suction chamber 12 includes a connection part 123 adapted to connect the extension part 121 and the first coupling part 122 to each other. The connection part 123 is a pipe adapted to allow the second suction hole 121a and the third suction hole 122a to vertically communicate with each other. In this case, the inner diameter of the connection part 123 is smaller than that of the third suction hole 122a and is the same as the second suction hole 121a.

On the other hand, the extension part 121, the first coupling part 122, and the connection part 123 constituting the suction chamber 12 are formed unitarily with one another by means of injection molding (or double injection molding) using a single mold, and otherwise, they are made independently by means of injection molding and coupled to one another by means of screw fastening.

As shown in FIG. 3, the first coupling part 122 includes a first connector 122-1 coupled to the top periphery of the backflow prevention unit 13 and having the third suction hole 122a formed on the lower portion of the inner peripheral surface thereof in such a manner as to be aligned vertically to the second suction hole 121a to communicate with the second suction hole 121a and a second connector 122-2 disposed to surround the outer periphery of the first connector 122-1 therewith in such a manner as to be spaced apart from the first connector 122-1 by a given distance and coupled to the top periphery of the storage vessel 14. At this time, the first connector 122-1 and the second connector 122-2 have screw threads formed along the inner peripheral surfaces thereof in such a manner as to be screw-fastened to the outer peripheral surfaces of the backflow prevention unit 13 and the storage vessel 14.

As shown in FIGS. 2 and 3, the backflow prevention unit 13 is coupled to the first coupling part 122 in a vertical direction thereof. That is, the backflow prevention unit 13 is disposed in a vertical direction with respect to the adsorption surface 111 of the adsorption unit 11. The backflow prevention unit 13 includes a second coupling part 131 screw-fastened to the first connector 122-1 of the first coupling part 122 and a pair of backflow prevention films 132 disposed on the underside of the second coupling part 131 to prevent the breast milk stored in the storage vessel 14 from flowing back to the suction chamber 12.

As shown in FIGS. 2 and 3, the backflow prevention films 132 are relatively thin films made of, for example, a silicone material and serve to close the space between the storage vessel 14 and the suction chamber 12 or release the closed state in accordance with the operation of the electric pump 1. For example, if a suction force is generated by means of the electric pump 1, the backflow prevention films 132 come into close contact with each other to close the space between the storage vessel 14 and the suction chamber 12, and if the breast pump is in a compressed state (in a non-suction state), the closed state is released to move the pumped breast milk to the storage vessel 14.

The storage vessel 14 is a breast milk bottle for storing the breast milk pumped from the mother's breast and is screw-fastened to the second connector 122-2 of the first coupling part 122 along the top periphery thereof. If the breast milk is fully stored in the storage vessel 14, the storage vessel 14 is separated from the suction chamber 12 and kept at a given place.

As shown in FIG. 2, the storage vessel 14 has scales 14 indicated on the outer peripheral surface thereof to check the quantity of breast milk stored therein. Even if not shown, a temperature sensor may be disposed on one side of the storage vessel 14 to sense the temperature of the breast milk stored therein. At this time, the temperature sensor may be a state change temperature sensor (a record label for displaying the changes of temperature with colors).

According to the present invention, the storage vessel 14 is the breast milk bottle, but instead of the breast milk bottle, a breast milk pack can be used. At this time, the inlet of the breast milk pack is fitted surroundingly to the outer peripheral surface of the second connector 122-2 of the first coupling part 122 and then fixed thereto by means of an elastic band mounted on the outer peripheral surface of the second connector 122-2.

As shown in FIG. 3, the adsorption unit 11 further includes an alignment piece 113 formed on the rear side of the suction tank 112 in such a manner as to be fitted to an alignment groove 121-2 formed at the inside of the extension part 121 of the suction chamber 12.

The alignment piece 113 is configured to have at least one side thereof cut in a straight line, so that it has a generally semi-circular or semi-oval shape. Accordingly, the alignment groove 121-2 has a semi-circular or semi-oval shape. In the state where the alignment piece 113 is insertedly coupled to the alignment groove 121-2, the suction chamber 12 is fixed to the suction tank 112, without being rotated.

Figure 4:
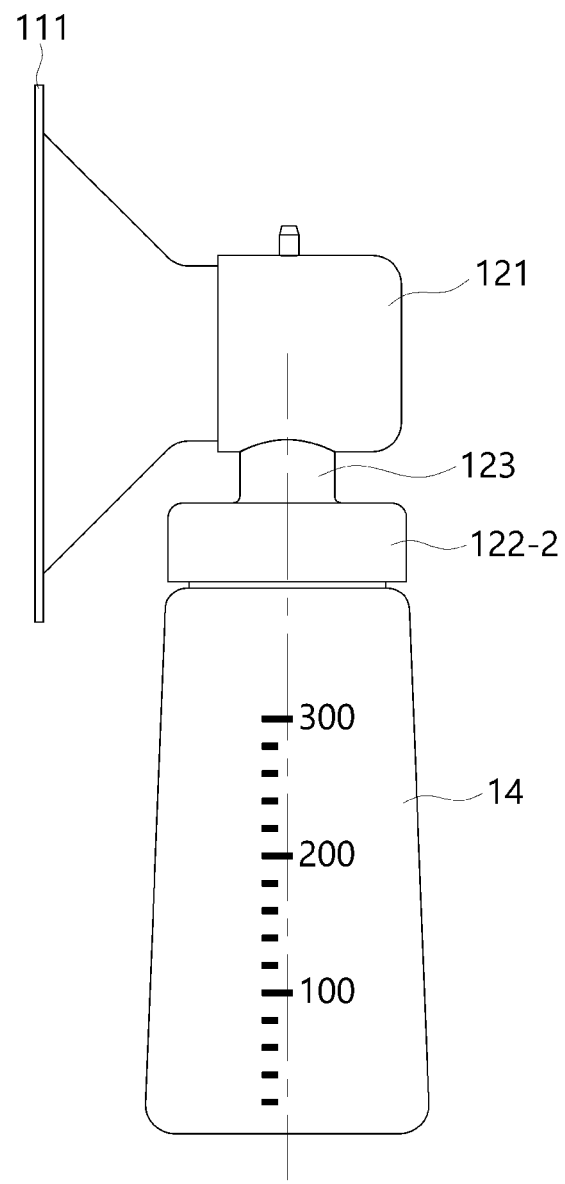
FIG. 4 is a side view showing the hands-free breast pump of FIG. 1.
Figure 5:
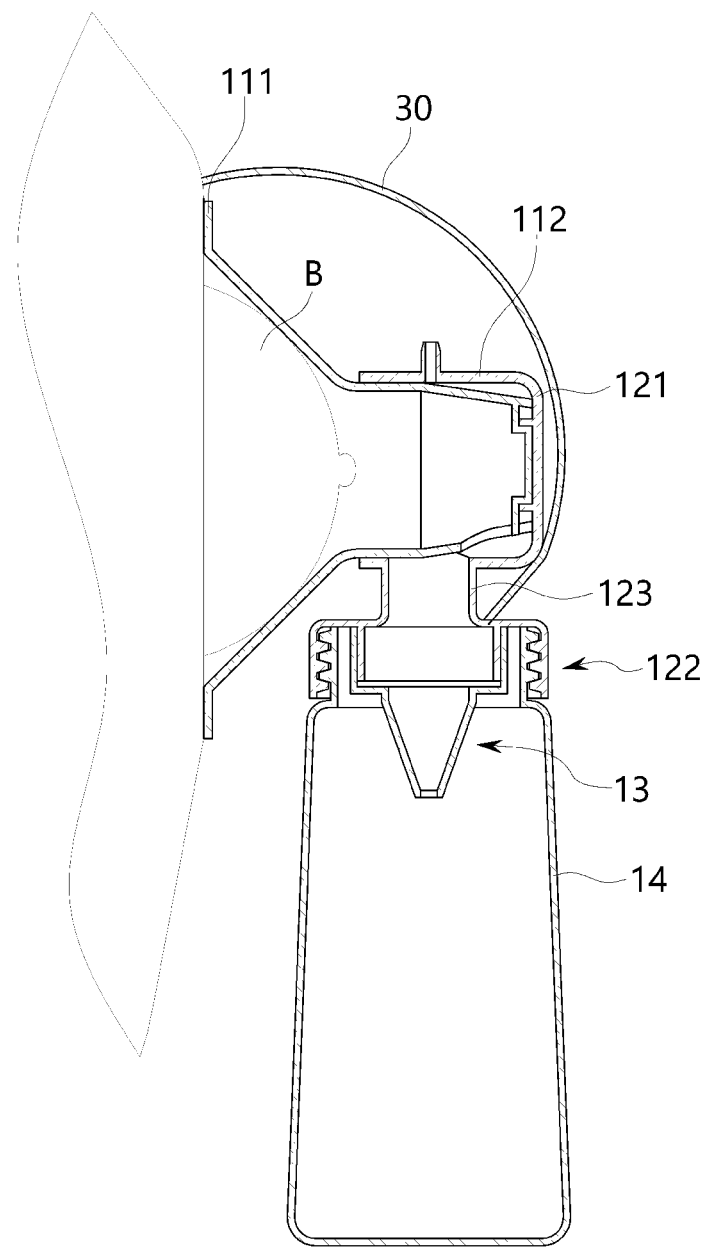
FIG. 5 is a side view showing the fixed state of the hands-free breast pump of FIG. 1 to a bra.

FIG. 4 is a side view showing the hands-free breast pump of FIG. 1, and FIG. 5 is a side view showing the fixed state of the hands-free breast pump of FIG. 1 to a bra.

Referring to FIGS. 4 and 5, the hands-free breast pump 10 according to the present invention is configured wherein the adsorption unit 11, the suction chamber 12, the backflow prevention unit 13 and the storage vessel 14 are coupled to one another. In this case, the suction chamber 12 is disposed in the vertical direction with respect to the adsorption surface 111 of the adsorption unit 11, and the storage vessel is disposed in a parallel direction to the adsorption surface 111. That is, the whole structure from the adsorption unit 11 to the storage vessel 14 has a generally '¬'-like shape, so that the hands-free breast pump 10 stably comes into close contact with the mother's breast and is fixed to her breast through a bra 30.

According to the conventional hands-free breast pumps, up to now, the coupling structure between the adsorption unit and the storage vessel does not have such '¬'-like shape and is thus inclined to a given angle, that is, to an angle of about 45°, so that if the conventional hands-free breast pumps are fixed to the breasts through bras, the adsorption unit and the storage vessel are bent, thereby being not stably supported against the bras. To the contrary, the hands-free breast pump 10 according to the present invention has the whole structure from the adsorption unit 11 to the storage vessel 14 having the shape of '¬', and the connection part 123 has a smaller outer diameter than the extension part 121 and the first coupling part 122 to form a neck portion of the breast pump 10, so that the lower end portion of the bra 30 is fitted to the connection part 123, thereby allowing the hands-free breast pump 10 to be stably fixed to the mother's breast.

Figure 6:
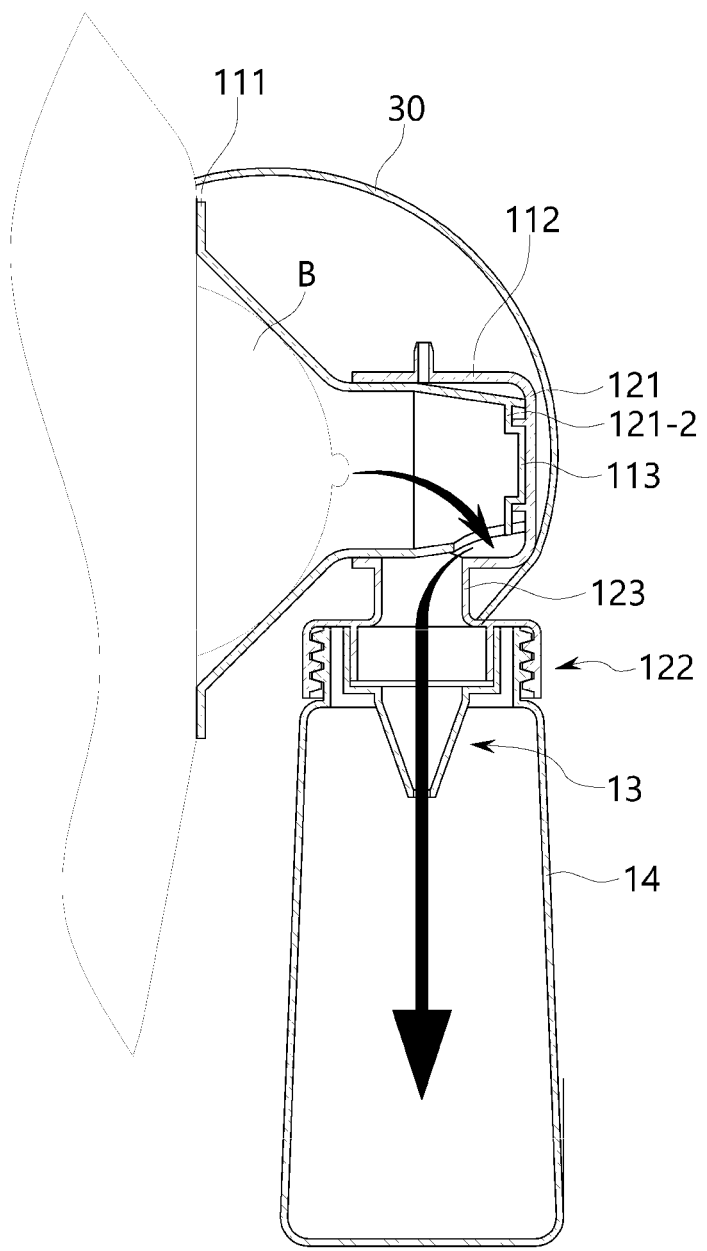
FIG. 6 is a side view showing a breast pumping passage of breast milk pumped through the hands-free breast pump according to the present invention wherein the pumped breast milk is discharged from an adsorption unit to a storage vessel.
Figure 7:
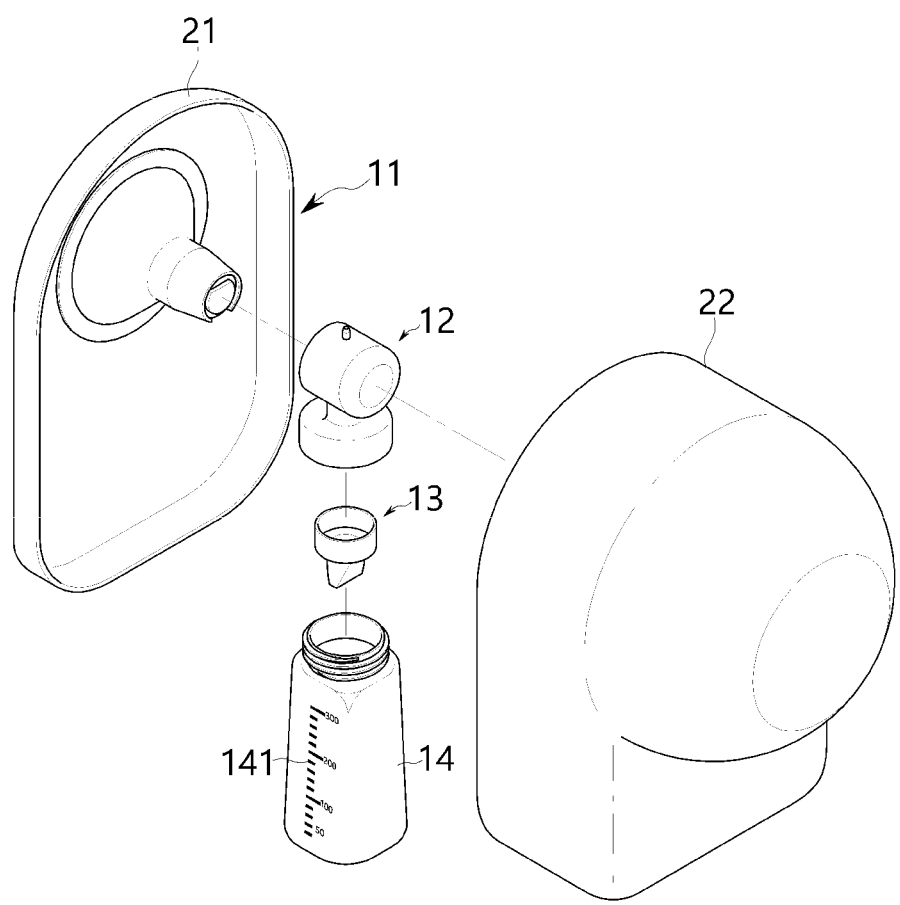
FIG. 7 is a perspective view showing the hands-free breast pump of FIG. 6 coupled to an electric pump.

FIG. 6 is a side view showing a breast pumping passage of breast milk pumped through the hands-free breast pump according to the present invention wherein the pumped breast milk is discharged from the adsorption unit to the storage vessel, and FIG. 7 is a perspective view showing the hands-free breast pump of FIG. 6 coupled to the electric pump.

Referring to FIGS. 2, 6 and 7, if the electric pump 1 operates to allow the interior of the suction chamber 12 to become in a vacuum or air pressure state, the adsorption unit 11 inserted into the suction chamber 12 becomes compressed, and accordingly, the breast B is stimulated by means of the adsorption unit 11 to express the breast milk therefrom. The breast milk expressed from the breast B is then passed through the first suction hole 112a of the suction tank 112 and the second suction hole 122a and discharged to the storage vessel 14 through the backflow prevention unit 13.

That is, the suction force of the electric pump 1 is transmitted sequentially to the suction line 2, the suction chamber 12, the adsorption unit 11, and the breast B and thus stimulates the breast B periodically, thereby conducting the breast pumping. At this time, the pair of backflow prevention films 132 of the backflow prevention unit 13 comes into close contact with each other to close the space between the suction chamber 12 and the storage vessel 14, so that the breast milk expressed from the breast B is temporarily collected to the adsorption unit 11 and the space above the backflow prevention films 132. In this state, if the suction force disappears and a compressive force is generated by the operation of the electric pump 1, the backflow prevention films 132 are isolated from each other by means of the compressive force, the pumped breast milk is discharged to the interior of the storage vessel 14 and stored therein.

According to the present invention, on the other hand, the electric pump 1 includes a display window 1-1, a plurality of control buttons 1-2, and a controller (not shown). Further, the electric pump 1 includes a lamp for displaying an operating state.

For example, the display window 1-1 is an LCD window which displays an operating state of the electric pump 1, breast pumping time, and the quantity of breast milk pumped. Also, the display window 1-1 displays a vacuum pressure, a breast milk temperature measured by a separate temperature sensor (which is disposed on the storage vessel or suction line), and the like.

The plurality of control buttons 1-2 include a power button, a stop button, a vacuum pressure control button for controlling the size of the vacuum pressure, a breast pumping time control button for controlling the breast pumping time, and a breast pumping time or pumped breast milk quantity setting button.

The controller controls the operation of the electric pump 1 in response to the plurality of control buttons 1-2. For example, the controller calculates the quantity of breast milk pumped on the basis of the breast pumping time and the strength of the vacuum pressure to display the calculated result on the display window 1-1. Further, the controller allows the temperature sensed through the temperature sensor to be displayed in real time on the display window 1-1.

Figure 8:
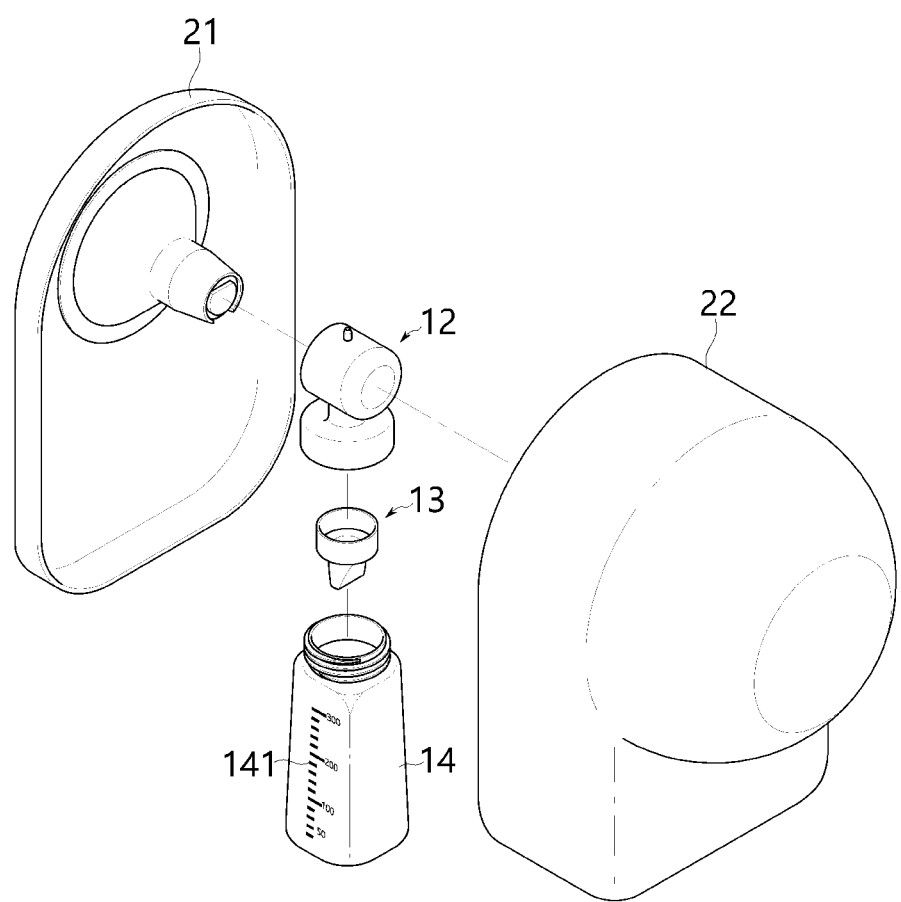
FIG. 8 is an exploded perspective view showing a hands-free breast pump according to a second embodiment of the present invention.
Figure 9:
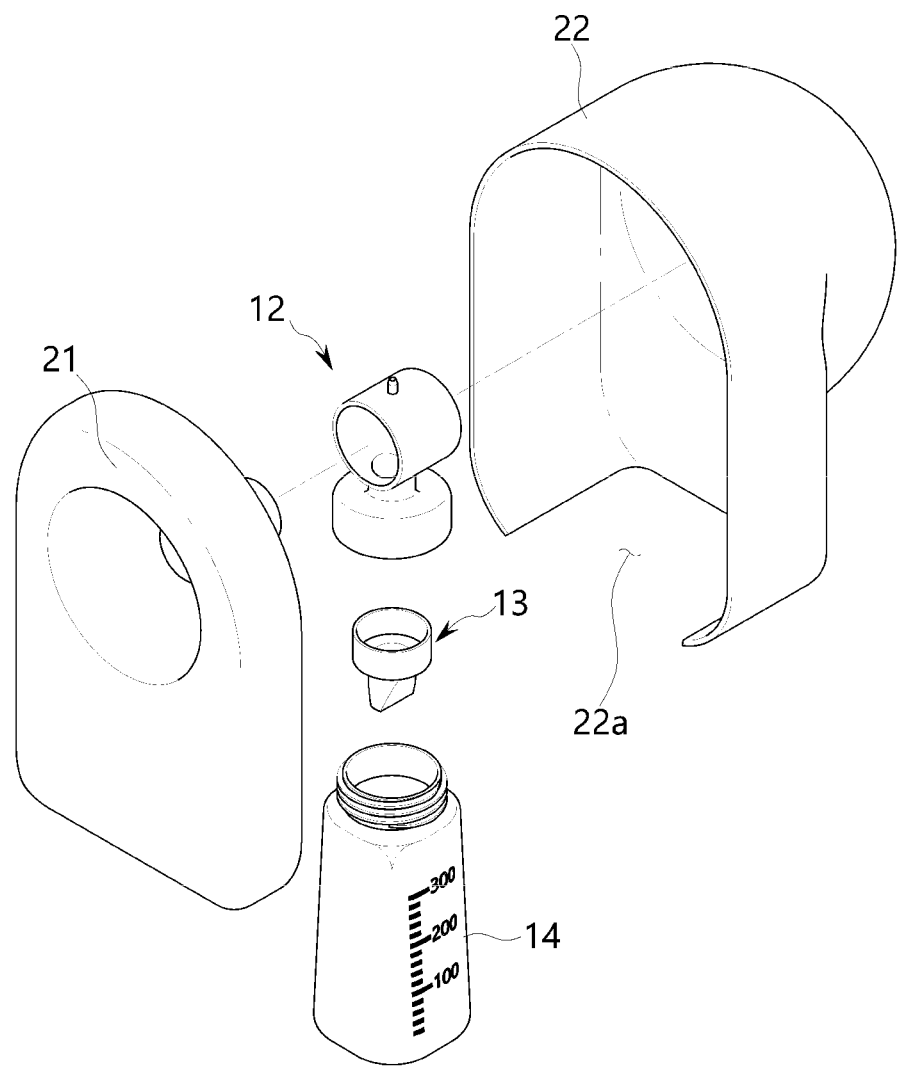
FIG. 9 is a perspective view showing the hands-free breast pump of FIG. 8 seen on the different side from that of FIG. 8.
Figure 10:
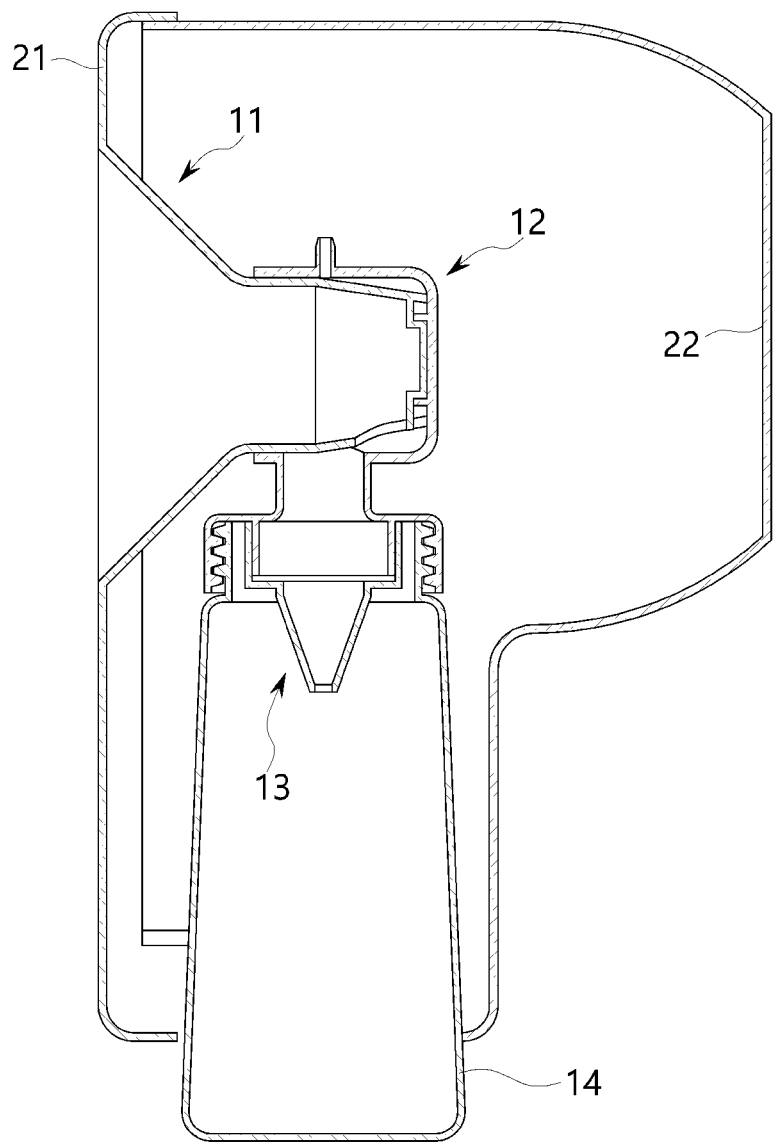
FIG. 10 is a sectional view showing the assembled state of the hands-free breast pump of FIG. 8.
Figure 11:
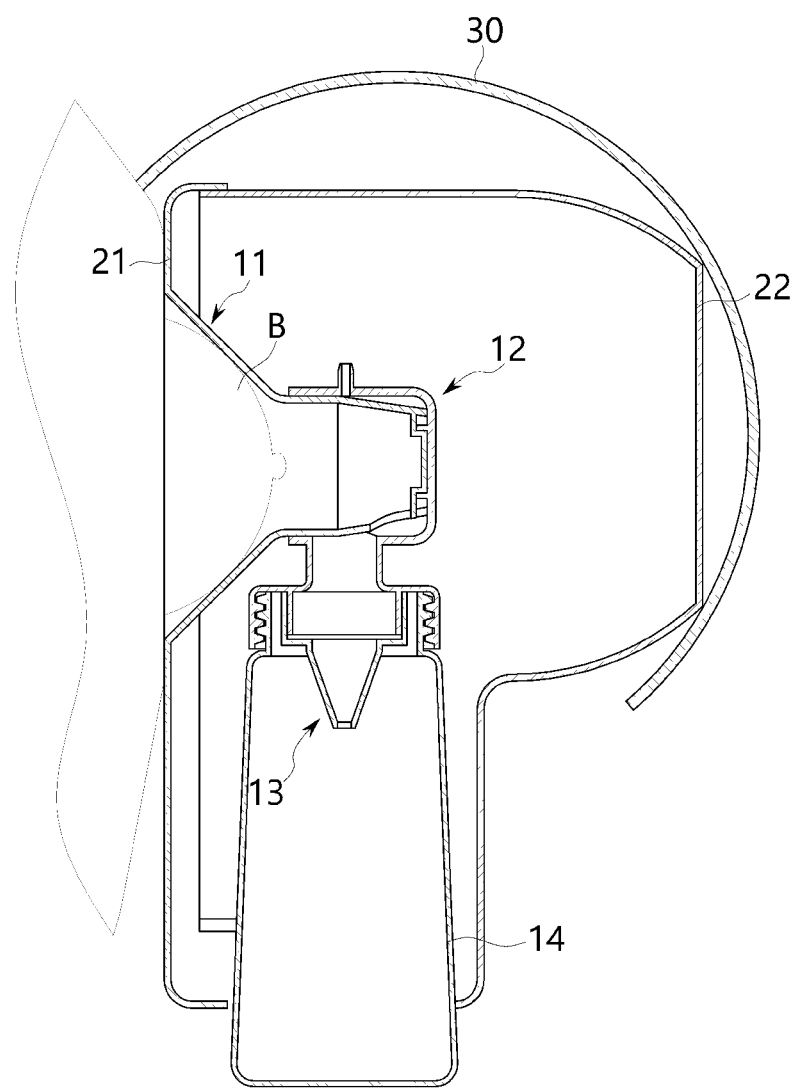
FIG. 11 is a side view showing the fixed state of the hands-free breast pump of FIG. 8 to a bra.

FIG. 8 is an exploded perspective view showing a hands-free breast pump according to a second embodiment of the present invention, FIG. 9 is a perspective view showing the hands-free breast pump of FIG. 8 seen on the different side from that of FIG. 8, FIG. 10 is a sectional view showing the assembled state of the hands-free breast pump of FIG. 8, and FIG. 11 is a side view showing the fixed state of the hands-free breast pump of FIG. 8 to a bra.

Referring to FIGS. 8 to 11, a hands-free breast pump according to a second embodiment of the present invention includes the adsorption unit 11, the suction chamber 12, the backflow prevention unit 13 and the storage vessel 14, like the hands-free breast pump 10 as shown in FIGS. 1 to 3, and operates in the same manner as the hands-free breast pump 10. However, the hands-free breast pump according to the second embodiment of the present invention further includes a front cover 21 and a rear cover 22.

In more detail, the hands-free breast pump according to the second embodiment of the present invention includes the rear cover 22 having a given curved surface formed on the portion surrounded with the bra 30 to prevent the bra 30 from being distorted correspondingly to the shape of the rear portion of the suction chamber 12 when the rear portion of the suction chamber 12 is fixed to the bra 30, thereby improving the outer appearance, and the front cover 21 adapted to detachably couple the rear cover 22 thereto.

As shown in FIG. 8, the front cover 21 is coupled to the adsorption unit 11 on the center thereof. Since the front surface of the front cover 21 is attached tightly to the mother's breast, it is made of a relatively soft material to prevent foreign body sensation and pain upon compression from occurring, and the rear surface of the front cover 21 is made of a relatively hard material in such a manner as to be coupled stably to the rear cover 22. For example, the front cover 21 is made of a synthetic resin (plastic) having relatively high stiffness and has soft silicone rubber laid on the front surface thereof.

As shown in FIGS. 9 and 11, the rear cover 22 has the given curved surface formed on the rear portion thereof and includes an insertion slot 22*a* formed on the lower portion thereof in such a manner as to insert the storage vessel 14 thereinto in the state where the front cover 21 and the rear cover 22 are coupled to each other and to allow the storage vessel 14 to be stably coupled to the second connector 122-2 of the first coupling part 122. The rear cover 22 is made of a synthetic resin (plastic) having relatively high stiffness, so that even if the rear portion of the rear cover 22 is fixed to the bra 30, the rear cover 22 is not changed in shape.

The hands-free breast pump according to the second embodiment of the present invention is configured wherein the rear cover 22 having the given curved surface is disposed on the rear side portion of the breast pump fixed by the bra 30. Accordingly, when the bra 30 is fixed to the breast pump, the curved surface (having a shape of a peak) of the rear cover 22 is projected onto the bra 30, so that the bra 30 has the shape of the peak when viewed from the front side of the mother, thereby improving the outer appearance of the breast pump.

Figure 12:
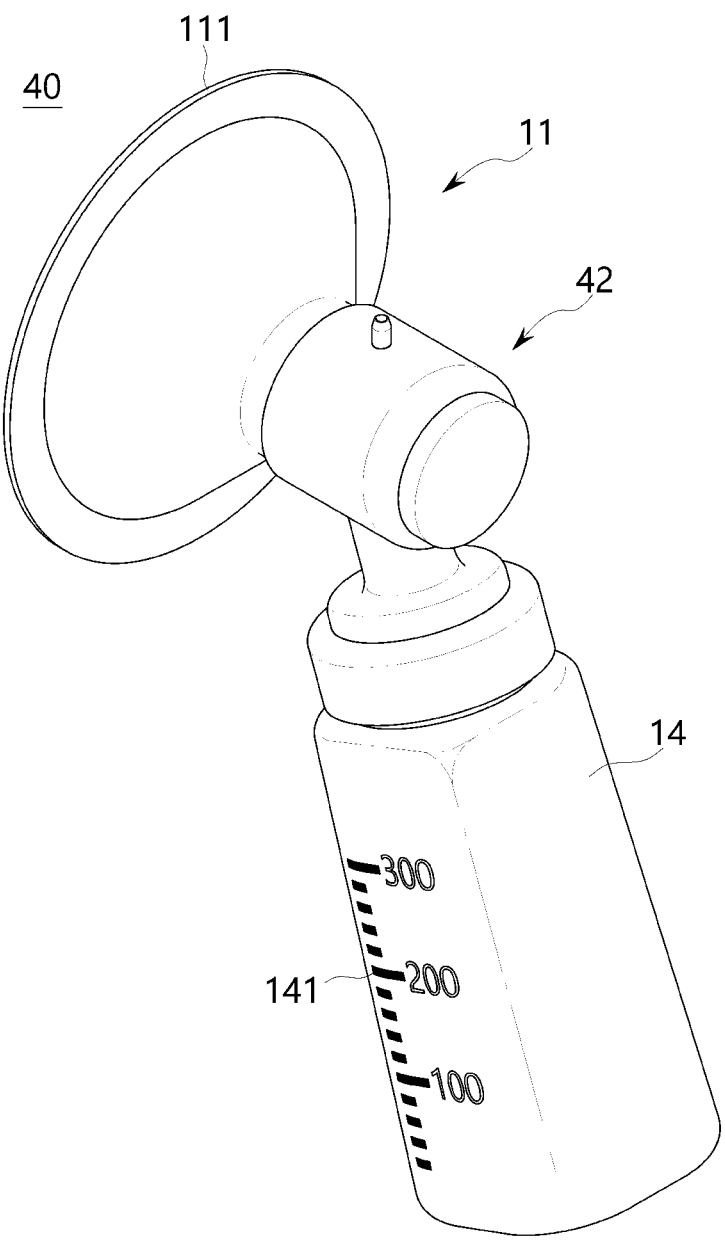
FIG. 12 is a perspective view showing the assembled state of a hands-free breast pump according to a third embodiment of the present invention.
Figure 13:
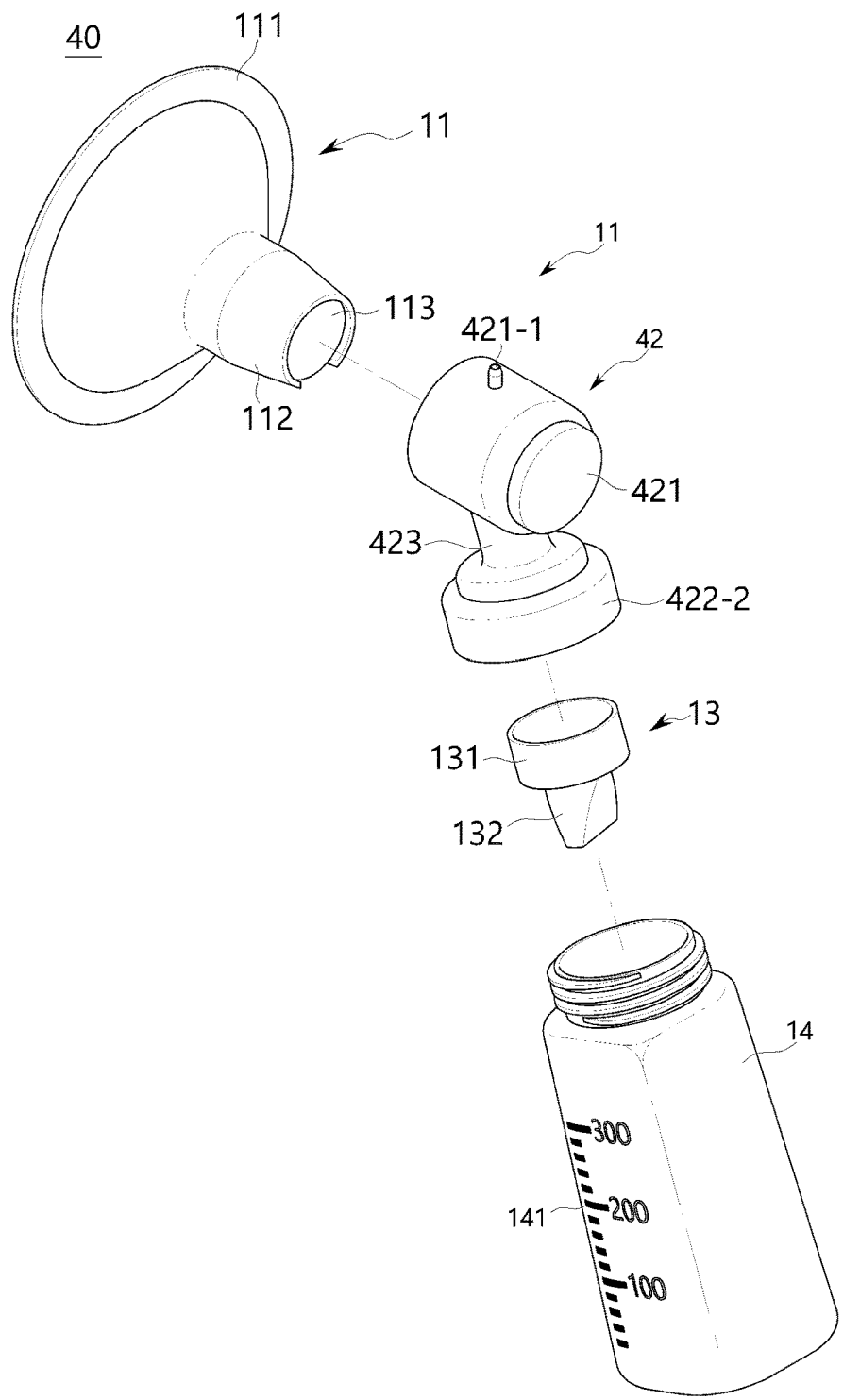
FIG. 13 is an exploded perspective view showing the hands-free breast pump of FIG. 12.
Figure 14:
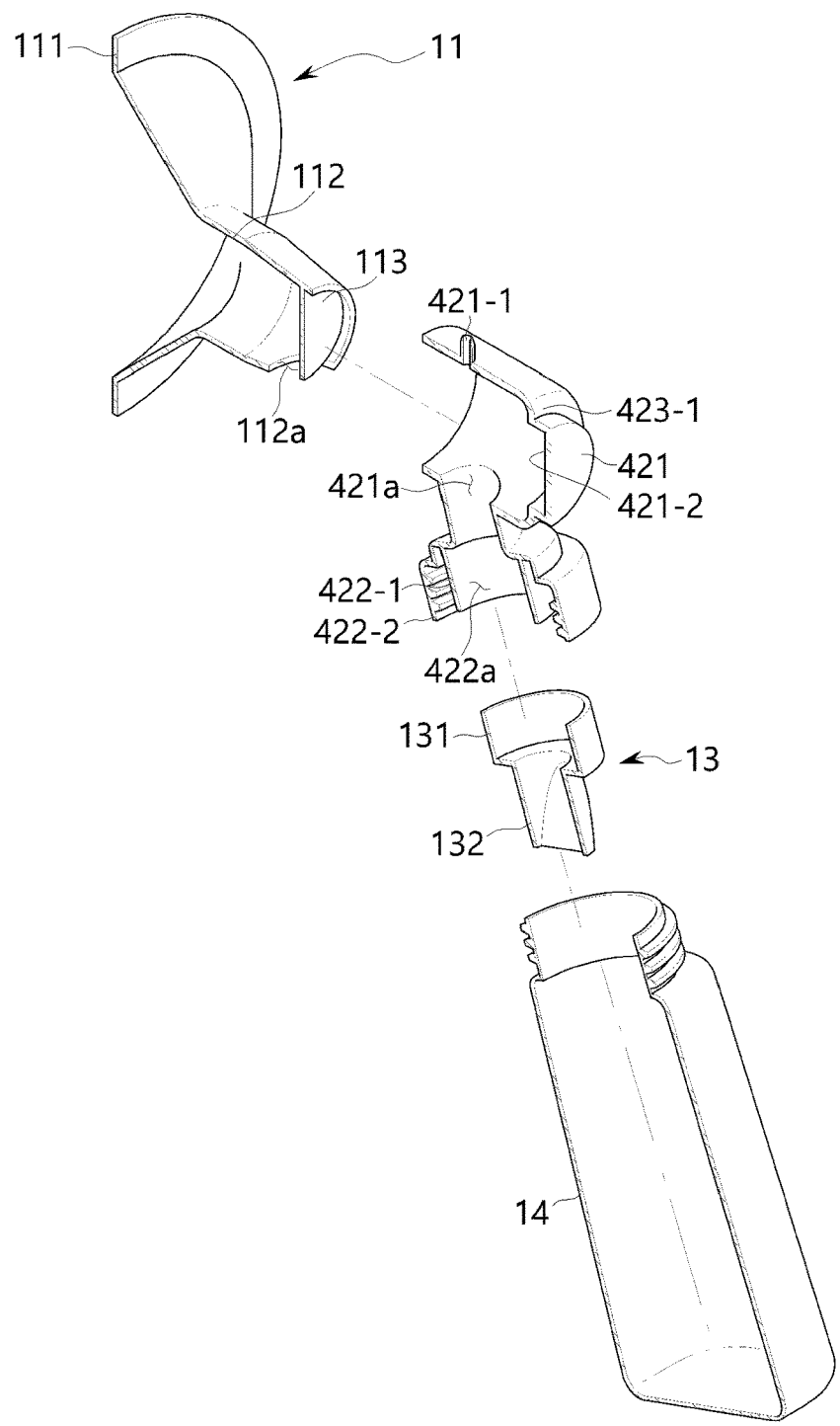
FIG. 14 is a sectional perspective view showing the hands-free breast pump of FIG. 13 cut off in an up and down direction thereof.

FIG. 12 is a perspective view showing the assembled state of a hands-free breast pump according to a third embodiment of the present invention, FIG. 13 is an exploded perspective view showing the hands-free breast pump of FIG. 12, and FIG. 14 is a sectional perspective view showing the hands-free breast pump of FIG. 13 cut off in an up and down direction thereof.

In the same manner as the hands-free breast pump 10 according to the first embodiment of the present invention, as shown in FIGS. 12 to 14, a hands-free breast pump 40 according to a third embodiment of the present invention includes an adsorption unit 11, a suction chamber 42, a backflow prevention unit 13 and a storage vessel 14. In this case, the structure of the suction chamber 42 of the hands-free breast pump 40 according to the third embodiment of the present invention is different from that of the hands-free breast pump 10 according to the first embodiment of the present invention, and accordingly, the suction chamber 42 will be in detail explained hereinafter.

As shown in FIGS. 13 and 14, the suction chamber 42 of the hands-free breast pump 40 according to the third embodiment of the present invention includes an extension part 421 in the same manner as the suction chamber 12 of the hands-free breast pump 10 according to the first embodiment of the present invention.

The extension part 421 having a connection pipe 421-1 disposed on one side of the top portion thereof in such a manner as to be connected to the suction line 2 (see FIG. 7) and a second suction hole 421*a* formed on the lower portion of the inner peripheral surface thereof in such a manner as to communicate with the first suction hole 112*a* of the suction tank 112.

As shown in FIG. 14, the suction chamber 42 includes a first coupling part 422 extended downwardly from the extension part 121 in such a manner as to be coupled to the backflow prevention unit 13 and the storage vessel 14 and having a third suction hole 422*a* formed on the lower portion of the inner peripheral surface thereof in such a manner as to communicate with the second suction hole 421*a*. Further, as shown in FIG. 13, the suction chamber 42 includes a connection part 423 disposed backwardly on the lower portion of the extension part 421 in such a manner as to be inclined by a given angle of about 20 to 50°, desirably, 30 to 45°, to connect the extension part 421 and the first coupling part 422 to each other.

As shown in FIG. 14, the connection part 423 is a pipe disposed backwardly on the lower portion of the extension part 421 in such a manner as to be inclined by a given angle of about 20 to 50°, desirably, 30 to 45°, to allow the second suction hole 421*a* to communicate with the third suction hole 422a. The outer diameter of the connection part 423 is smaller than the inner diameter of the third suction hole 422a and the inner diameter of the connection part 423 is the same as the inner diameter of the second suction hole 421a.

Further, as shown in FIG. 14, the connection part 423 further includes a locking groove 423-1 inwardly concaved on the back of the outer peripheral surface thereof in such a manner as to lockedly insert the lower end portion of the bra 30 thereinto. Accordingly, the lower end portion of the bra 30 is inserted and locked on the locking groove 423-1 of the connection part 423, the breast pump 40 can be stably fixed to the breast by means of the elasticity of the bra 30.

On the other hand, the extension part 421, the first coupling part 422, and the connection part 423 constituting the suction chamber 42 are formed unitarily with one another by means of injection molding (or double injection molding) using a single mold, and otherwise, they are made independently by means of injection molding and coupled to one another by means of screw fastening.

As shown in FIG. 13, the first coupling part 422 includes a first connector 422-1 coupled to the top periphery of the backflow prevention unit 13 and having the third suction hole 422a formed on the lower portion of the inner peripheral surface thereof in such a manner as to be aligned vertically to the second suction hole 421a to communicate with the second suction hole 421a and a second connector 422-2 disposed to surround the outer periphery of the first connector 422-1 therewith in such a manner as to be spaced apart from the first connector 422-1 by a given distance and coupled to the top periphery of the storage vessel 14. At this time, the first connector 422-1 and the second connector 422-2 have screw threads formed along the inner peripheral surfaces thereof in such a manner as to be screw-fastened to the outer peripheral surfaces of the backflow prevention unit 13 and the storage vessel 14.

Figure 15:
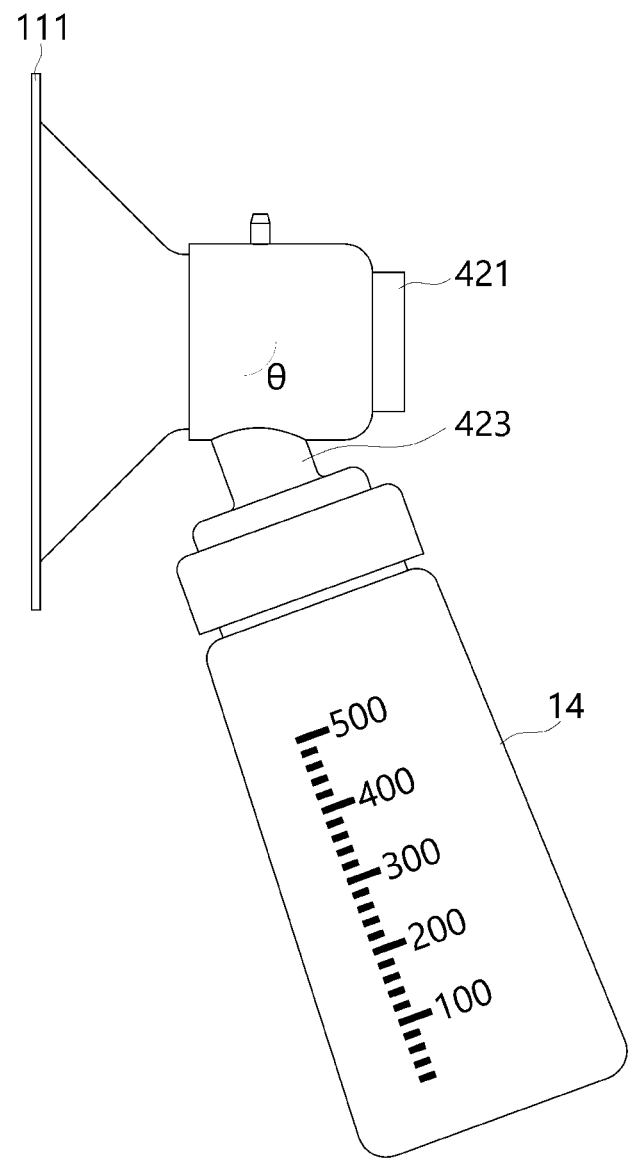
FIG. 15 is a side view showing the hands-free breast pump of FIG. 12.
Figure 16:
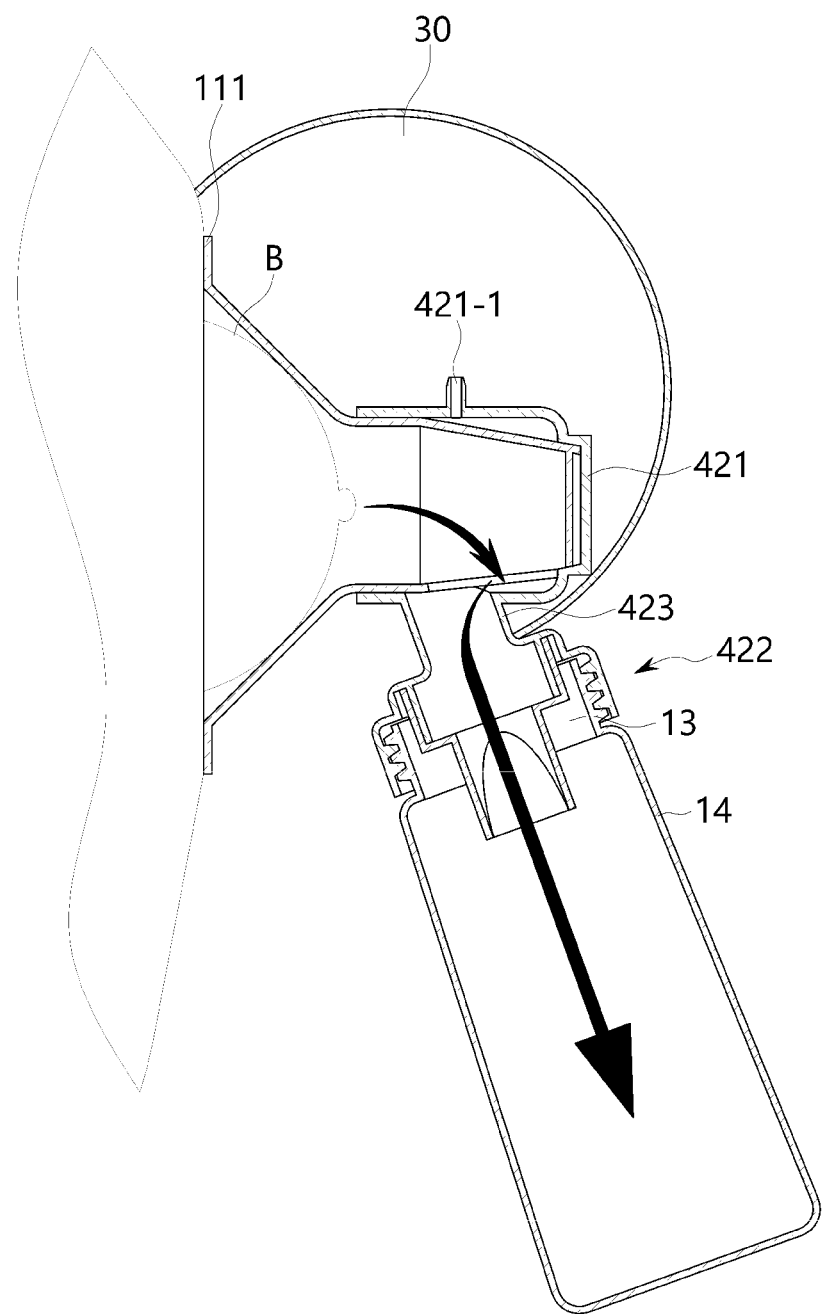
FIG. 16 is a side view showing the fixed state of the hands-free breast pump of FIG. 12 to a bra.

FIG. 15 is a side view showing the hands-free breast pump of FIG. 12, and FIG. 16 is a side view showing the fixed state of the hands-free breast pump of FIG. 12 to a bra.

Referring to FIGS. 15 and 16, the hands-free breast pump 40 according to the third embodiment of the present invention is configured to couple the adsorption unit 11, the suction chamber 42, the backflow prevention unit 13 and the storage vessel 14 to one another, wherein the connection part 423 of the suction chamber 42 is disposed backwardly on the lower portion of the extension part 421 in such a manner as to be inclined by the given angle of about 20 to 50°, desirably, 30 to 45°. That is, the connection part 423 of the suction chamber 42 is disposed inclined by the given angle of about 20 to 50° with respect to the adsorption surface 111. At this time, the connection part 423 further includes the locking groove 423-1 inwardly concaved on the back of the outer peripheral surface thereof in such a manner as to lockedly insert the lower end portion of the bra 30 thereinto, so that the lower end portion of the bra 30 is stably locked on the locking groove 423-1 of the connection part 423 to allow the breast pump 40 to come into close contact with the breast.

In the same manner as the hands-free breast pump according to the second embodiment of the present invention. On the other hand, the hands-free breast pump 40 according to the third embodiment of the present invention includes the front cover 21 and the rear cover 22 as shown in FIGS. 8 and 9. According to the third embodiment of the present invention, at this time, the storage vessel 14 is disposed inclined backwardly by a given angle, so that the insertion slot 22a of the rear cover 22 is formed on the lower portion of the rear cover 22 and is also extended to the rear side of the rear cover 22 from the lower portion thereof in correspondence with the arrangement of the storage vessel 14.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

INDUSTRIAL APPLICABILITY

The present invention is applicable to the field of a breast pump.

The invention claimed is:

1. A hands-free breast pump comprising:
a funnel-shaped adsorption unit having an adsorption surface adapted to come into contact with a mother's breast and a suction tank protruding backwardly from the adsorption surface in a vertical direction with respect to the adsorption surface and having a first suction hole formed on a lower portion of an inner peripheral surface thereof in a horizontal direction with respect to the adsorption surface;
a suction chamber having an extension part adapted to be insertingly coupled to a rear portion of the suction tank, the extension part having a connection pipe disposed on one side of a top portion thereof in such a manner as to be connected to a suction line and a second suction hole formed on the lower portion of the inner peripheral surface thereof in such a manner as to be formed in a horizontal direction with respect to the adsorption surface or formed inclined backwardly by a given angle of about 20 to 50°, and a first coupling part extended downwardly from the extension part and having a third suction hole formed thereon to communicate with the second suction hole;
a backflow prevention unit coupled to the lower periphery of the first coupling part; and
a storage vessel coupled to the lower periphery of the first coupling part in such a manner as to be disposed in parallel with the adsorption surface in the horizontal direction with the adsorption surface or to be disposed inclined backwardly by a given angle of about 20 to 50° from the adsorption surface so as to store breast milk discharged from the backflow prevention unit therein,
wherein the first coupling part comprises a first connector having the third suction hole and a second connector disposed to surround an outer periphery of the first connector therewith in such a manner as to be spaced apart from the first connector by a given distance and coupled to a top periphery of the storage vessel, and the backflow prevention unit comprises a second coupling part screw-fastened to the first connector and a pair of backflow prevention films disposed on an underside of the second coupling part to prevent the breast milk stored in the storage vessel from flowing back to the suction chamber.

2. The hands-free breast pump according to claim 1, wherein the adsorption unit further comprises an alignment piece formed on a rear side of the suction tank in such a manner as to be fitted to an alignment groove formed at an inside of the extension part of the suction chamber, the alignment piece having a generally semi-circular or semi-oval shape, and correspondingly, the alignment groove having a semi-circular or semi-oval shape, so that in the state where the alignment piece is insertedly coupled to the alignment groove, the suction chamber is fixed to the suction tank, without being rotated.

3. The hands-free breast pump according to claim 1, wherein the suction chamber comprises a connection part adapted to connect the extension part and the first coupling part to each other in such a manner as to allow the second suction hole and the third suction hole to vertically communicate with each other, an outer diameter of the connection part being smaller than an inner diameter of the third suction hole and an inner diameter of the connection part being the same as an inner diameter of the second suction hole.

4. The hands-free breast pump according to claim 1, further comprising:
   a front cover coupled to the adsorption unit on a center thereof; and
   a rear cover having a front surface detachably coupled to a rear surface of the front cover and the rear surface having a given curved surface, the rear cover having an insertion slot formed on a lower portion thereof in such a manner as to insert the storage vessel thereinto in the state where the front cover and the rear cover are coupled to each other and to allow the storage vessel to be coupled to the first coupling part.

* * * * *